US006326794B1

(12) United States Patent
Lundquist et al.

(10) Patent No.: US 6,326,794 B1
(45) Date of Patent: Dec. 4, 2001

(54) METHOD AND APPARATUS FOR IN-SITU MONITORING OF ION ENERGY DISTRIBUTION FOR ENDPOINT DETECTION VIA CAPACITANCE MEASUREMENT

(75) Inventors: Paul Matthew Lundquist, San Jose; Son Van Nguyen, Los Gatos; Manmohanjit Singh, San Jose, all of CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/231,043

(22) Filed: Jan. 14, 1999

(51) Int. Cl.[7] .......................... G01R 27/26; G01N 27/62
(52) U.S. Cl. ............................. 324/678; 324/464
(58) Field of Search ...................... 324/686, 663, 324/658, 668, 459, 460, 678, 464

(56) References Cited

U.S. PATENT DOCUMENTS

| 4,689,869 | 9/1987 | Jambotkar et al. |
| 5,081,421 | 1/1992 | Miller et al. |
| 5,173,474 | 12/1992 | Connell et al. |
| 5,198,072 | 3/1993 | Gabriel . |
| 5,221,442 | 6/1993 | Kawasumi et al. |
| 5,311,452 | 5/1994 | Yokota et al. |
| 5,338,390 | 8/1994 | Barbee et al. |
| 5,433,813 | 7/1995 | Kuwabara . |
| 5,456,788 | 10/1995 | Barbee et al. |
| 5,489,361 | 2/1996 | Barbee et al. |
| 5,500,073 | 3/1996 | Barbee et al. |
| 5,501,766 | 3/1996 | Barbee et al. |
| 5,582,746 | 12/1996 | Barbee et al. |
| 5,667,701 | 9/1997 | Sato et al. |
| 5,867,020 | * 2/1999 | Moore et al. ............... 324/686 |
| 5,936,413 | * 8/1999 | Booth et al. ............... 324/464 |
| 5,973,415 | * 10/1999 | Brenner et al. ............ 324/686 |

FOREIGN PATENT DOCUMENTS

| 07130809 A | 5/1995 | (EP) . |
| 06120173 A | 4/1994 | (JP) . |

OTHER PUBLICATIONS

T. Kinoshita, S. Ma, M. Hane and J. McVittie, 1996 Symposium on VLSI Technology Proceeding, pp. 188–189.

S. V. Nguyen, D. Perez, R. Craig, M. Straub, A. Ting, R. Hsiao, C. Hwang, D. Haney, T. Neumann, Proceeding of the Fall 1998 Electrochemical Society Meeting, Abstract No. 511.

D. Brown, Data Storage, Oct. 1998, pp. 43–48.

* cited by examiner

Primary Examiner—Safet Metjahic
Assistant Examiner—J Kerveros
(74) Attorney, Agent, or Firm—Altera Law Group, LLC

(57) ABSTRACT

A method and apparatus that provides in-situ monitoring of both the ion flux and the ion energy distribution of plasma processes to determine the endpoint of the etch process or the integrity and reproducibility of the deposition process where ion bombardment and energy distribution play critical roles in the process. A capacitance sensor is provided for measuring ion flux and ion distribution. At least one capacitance sensor is disposed within a plasma reactor at a first position for detecting ion flux emanating from a plasma within the plasma reactor. The capacitance sensor generates an ion flux measurement signal in response to the detection of the ion flux. Each of the at least one capacitance sensors is coupled to signal lines for routing an ion flux measurement signal outside the plasma reactor. A plurality of capacitance sensors may be formed as one of a plurality of rows of parts to be processed.

28 Claims, 4 Drawing Sheets

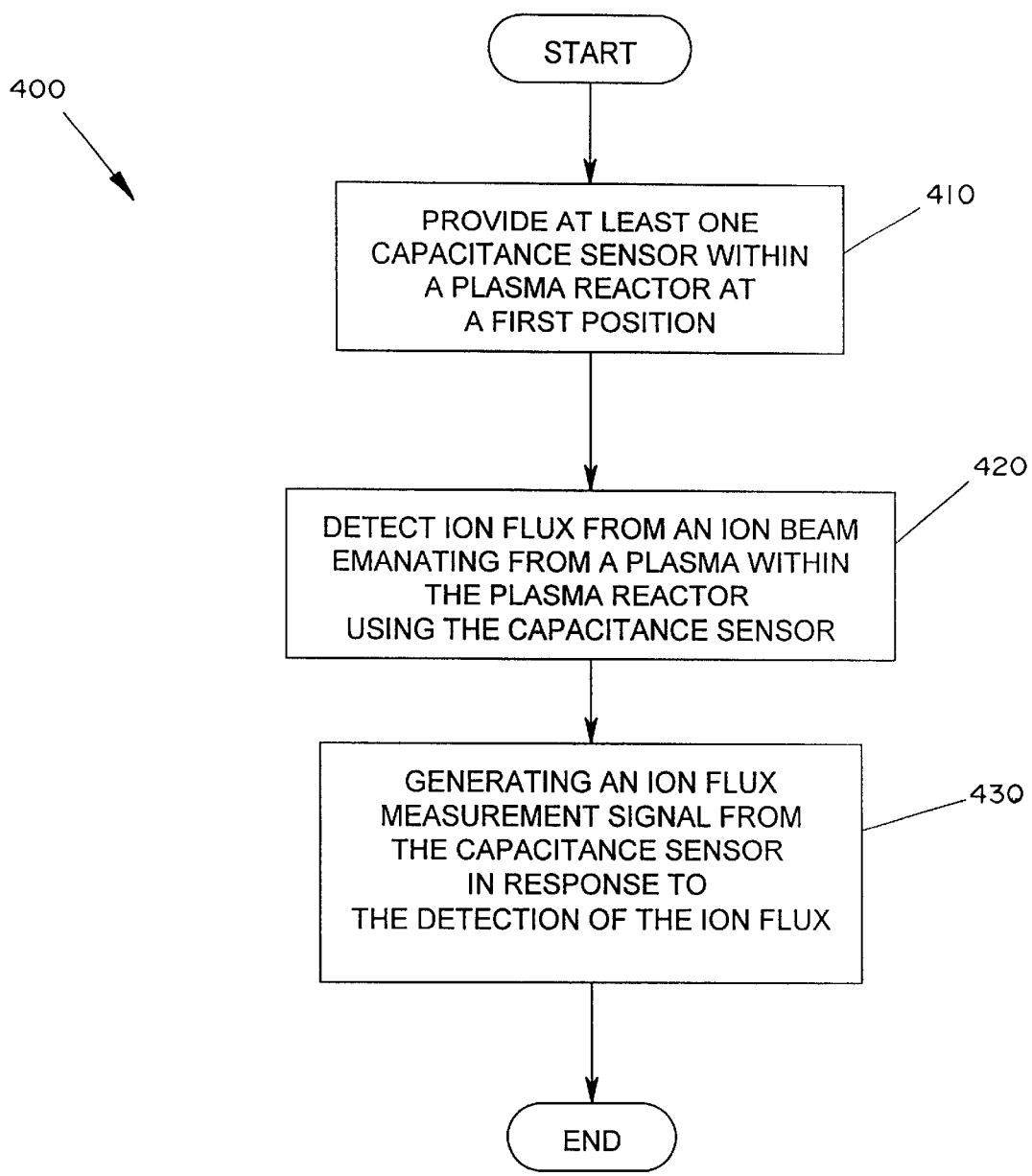

METHOD AND APPARATUS FOR IN-SITU MONITORING OF ION ENERGY DISTRIBUTION FOR ENDPOINT DETECTION VIA CAPACITANCE MEASUREMENT

BACKGROUND OF THE INVENTION

1. Field of the Invention

This invention relates in general to ion beam etching and deposition of thin film, and more particularly to a method and apparatus for in-situ monitoring of ion energy distribution for endpoint detection via capacitance measurement.

2. Description of Related Art

The processing of semiconductor wafers to create integrated circuits and devices such as sliders and disk overcoats involves a sequence of processing steps which build up or remove layer structures. These processing steps include the deposition of metals, dielectrics and semiconductor films, the creation of masks by lithography techniques, the doping of semiconductor layers by ion implantation and the etching of layers for selective or blanket material removal.

The semiconductor manufacturing industry continues to increase the functionality and performance of integrated circuits by increasing the number of circuit elements within each integrated circuits chip. Further, the size of devices structures continue to decrease. As the size of the elements decrease and their density increases, the processing steps become more critical. For example, wet etching techniques are generally inadequate for feature sizes less than 2 microns because wet etching is an isotropic process which etches equally well in all directions. With smaller feature sizes, the isotropic etching causes undesirable undercutting of the masking layer and possible destruction of closely spaced elements.

To address the need for a more anisotropic processes, ion beam and reactive ion etching and deposition are increasingly being used. These techniques involve the application of RF power to a cathode and typically allow the anode to electrically float. In either case, however, positive ions formed in the plasma are accelerated towards a wafer by a self-biased negative cathode to provide an effective anisotropic etch or deposition to the wafer.

Predicting or measuring when a desired layer of an element has been etched or deposited to the desired level is an important aspect of such ion beam and reactive ion etching processes. For example, it is desirable to measure when a layer of an element has been etched to a proper depth, i.e., when the etch process has reached an "end-point". Prediction or measurement of the end-point is needed to prevent damage to a wafer caused by excessive over-etching or to provide the proper etch depth. End-point detection is particularly crucial in ion beam and reactive ion etching, because this detection tends to have much lower selectivity than the comparable wet etching processes.

Prior end-point detection methods have typically monitored the emission spectra of the plasma, the surface layer of the wafer, or one of the operating parameters of the plasma system itself. For example, to form a reactive ion or ion beam, the equipment usually initiates and maintains a plasma in a gas mixture containing either fluorohydrocarbons or inert gas. The system maintains the plasma at a positive potential with respect to ground. Positive ions are then electrostatically extracted from the plasma to form a beam of energetic ions. Control of ion energy requires adjustment of the plasma potential, i.e., bias voltage, which is known as the beam (plasma) voltage. The beam of ions is then aimed at the substrate (normally remote from the plasma). Deposition and etch rates vary in proportion to the ion-beam (plasma) current density. With the gridded ion source, the gas flow, discharge voltage, beam voltage, beam current, accelerator voltage, and neutralization current can all be independently controlled over wide operating ranges. The specific type of gas used, its rate of flow into the ion source, and the magnitude of the discharge voltage will determine the ion species formed in the plasma. The beam voltage controls ion-impact energy at the substrate, for a given beam shape and beam/substrate geometry, the beam current controls the deposition and etch rate. The accelerator voltage can be used to adjust the beam shape, i.e., focus the beam, or adjust the beam's current density at the substrate.

Nevertheless, the stability of various plasma processes can be problematic. The intensity of an RF plasma can be difficult to control, and fluctuations lead to increased process tolerances or to decreased yields. The most important indicators of plasma deposition or etch rates are the flux of ions that strike the material surface, and the energy distribution of those ions. Optical and electronic techniques for monitoring plasma strengths are often utilized. However, these techniques are at best indirect methods and therefore do not provide adequate monitoring and measurement capabilities. The measurement of ion energy can be used to determine endpoint and uniformity of etch and deposition processes that use plasma.

It can be seen then that there is a need for a method and apparatus that provides in-situ monitoring of both the ion flux and the ion energy distribution of plasma processes.

SUMMARY OF THE INVENTION

To overcome the limitations in the prior art described above, and to overcome other limitations that will become apparent upon reading and understanding the present specification, the present invention discloses a method and apparatus that provides in-situ monitoring of both the ion flux and the ion energy distribution of plasma processes.

The present invention solves the above-described problems by providing a capacitance sensor for measuring ion flux and ion energy distribution at various locations in the ion beam or reactive ion etching chamber.

A system in accordance with the principles of the present invention includes least one capacitance sensor disposed within a plasma reactor at a first position for detecting ion flux emanating from a plasma within the plasma reactor and generating an ion flux measurement signal in response to the detection of the ion flux, each of the at least one capacitance sensor being coupled to signal lines for routing an ion flux measurement signal outside the plasma reactor.

Other embodiments of a system in accordance with the principles of the invention may include alternative or optional additional aspects. One such aspect of the present invention is that the at least one capacitance sensor comprises two conductors separated by at least one insulation layer.

Another aspect of the present invention is that the insulation layer comprises a dielectric material.

Another aspect of the present invention is that the signal lines are coupled to the two conductors.

Another aspect of the present invention is that the at least one capacitance sensor comprises a plurality of capacitance sensors formed as one of a plurality of rows of parts to be processed.

Another aspect of the present invention is that the at least one capacitance sensor is disposed in a pallet, the pallet providing support to a device being subjected to the ion beam.

Another aspect of the present invention is that the ion flux measurement signal represents a number of ions impinging a capacitance sensor.

Another aspect of the present invention is that at least one capacitance sensor comprises a plurality of capacitance sensors diffused within the electrode.

Another aspect of the present invention is that the plurality of capacitance sensors measure the ion distribution from the plasma.

Another aspect of the present invention is that the at least one capacitance sensor comprises a shape of a part to be processed to prevent a disturbance of the plasma.

Another aspect of the present invention is that the at least one capacitance sensor has an electric potential applied thereto for tuning the capacitance sensor to a predetermined energy range.

Another aspect of the present invention is that the electric potential is scanned to determine an energy distribution of the ions.

Another aspect of the present invention is that the at least one capacitance sensor is formed using a substance that is substantially identical to a part being processed.

These and various other advantages and features of novelty which characterize the invention are pointed out with particularity in the claims annexed hereto and form a part hereof. However, for a better understanding of the invention, its advantages, and the objects obtained by its use, reference should be made to the drawings which form a further part hereof, and to accompanying descriptive matter, in which there are illustrated and described specific examples of an apparatus in accordance with the invention.

BRIEF DESCRIPTION OF THE DRAWINGS

Referring now to the drawings in which like reference numbers represent corresponding parts throughout:

FIG. 4 is a flow chart of the method for in-situ monitoring of ion energy distribution for endpoint detection according to the present invention.

DETAILED DESCRIPTION OF THE INVENTION

In the following description of the exemplary embodiment, reference is made to the accompanying drawings which form a part hereof, and in which is shown by way of illustration the specific embodiment in which the invention may be practiced. It is to be understood that other embodiments may be utilized as structural changes may be made without departing from the scope of the present invention.

The present invention provides a method and apparatus that provides in-situ monitoring of both the ion flux and the ion energy distribution of plasma processes. More specifically, the present invention provides a plasma endpoint probe for in-situ monitoring of ion energy distribution for endpoint detection via capacitance measurement.

Figure 1:
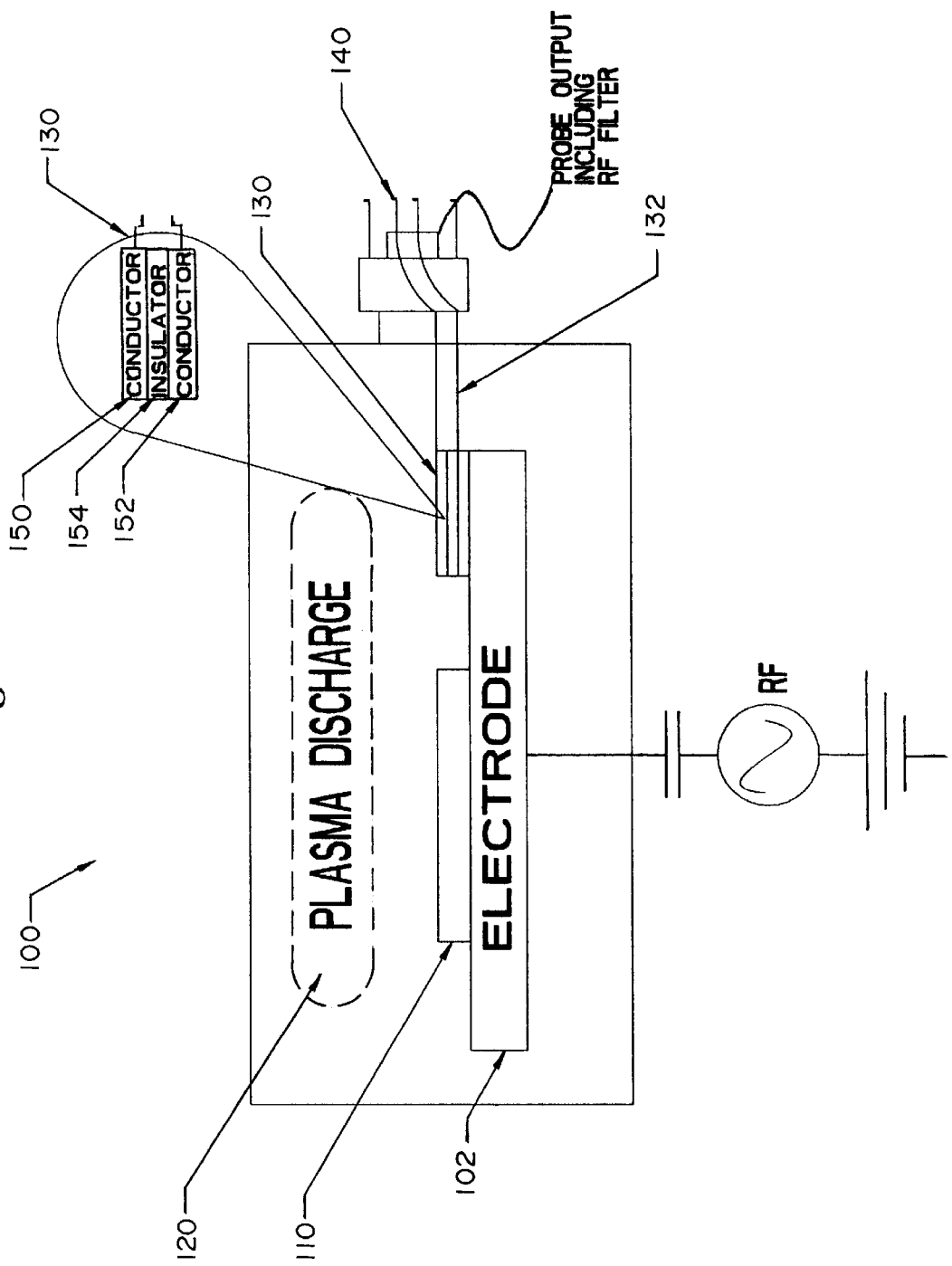
FIG. 1 illustrates a simplified diagram of the plasma reactor.

FIG. 1 illustrates a simplified diagram of the plasma reactor 100. In FIG. 1, an electrode 102 is provided in the plasma reactor 100. A target is positioned on the electrode 102 and a plasma discharge 120 provides ions that strike the material surface. Also shown in FIG. 1 is an Plasma Endpoint Probe (PEP) 130 for monitoring the ion flux and ion energy. The PEP 130 is a capacitance sensor that is disposed within the plasma reactor 100 at a position for detecting ion flux from an ion beam emanating from plasma 120 within the plasma reactor 100. The capacitance sensor 130 generates an ion flux measurement signal in response to the detection of the ion flux. The signal lines 132 route the ion flux measurement signal outside the plasma reactor 100 via the PEP interface 140.

Furthermore, the PEP 130 mimics the electrical environment of the parts that are being processed, so that the local disturbance to the plasma 120 caused by the PEP 130 is minimized. As illustrated in FIG. 1, the PEP 130 includes two conductors 150, 152 separated by at least one insulator layer 154, e.g., a dielectric material. Ions that strike the surface conductor 150 cause a potential difference across the dielectric layer 154. The measurement or monitoring of this voltage provide a direct measure of the flux or number of ions that strike the surface electrode. If an electric potential is applied across the two conductors 150, 152, the probe 130 can be tuned to select specific ion energy ranges. If this applied potential is scanned, the actual energy distribution of the ions can be determined along with the number of ions. The determination is a time averaging value measured over the period of oscillation of the applied potential. It is also a spatial averaging over the size of the surface electrode.

The two conductors 150, 152 are connected to signal lines 132 that provide signals at the PEP output through an interface 140. An RF filter (not shown) or other signal processing devices may be coupled at the PEP interface 140. The PEP 130 can in some cases be formed in the shape of a part to be processed, and thus inserted anywhere in the distribution of parts on the electrode 102 or on a pallet (see FIG. 3). The PEP 130 can also be formed as a part of the electrode 102. In this way, the strength of the plasma 120 can be monitored at any location of an electrode 102 or palette, or at several locations simultaneously.

Figure 2:
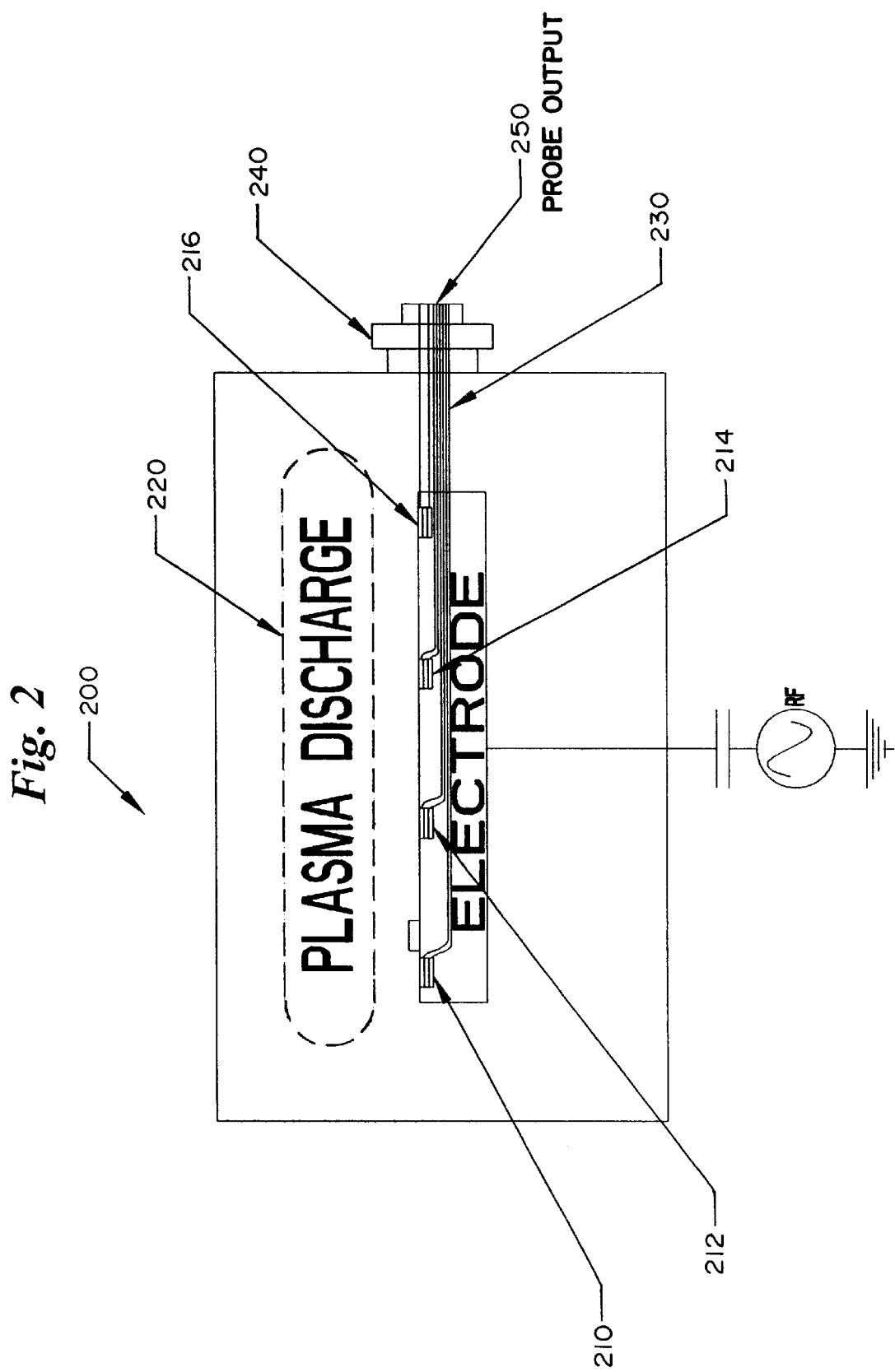
FIG. 2 illustrates a plurality of plasma electrode probes formed in the electrode for measuring energy distribution of ions and total energy on the surface of the electrode.

FIG. 2 illustrates a plasma reactor 200 including a second embodiment of the present invention. In FIG. 2, a plurality of plasma electrode probes 210–216 are formed and diffused in the electrode for measuring energy distribution of ions and total energy on the surface of the electrode. Each probe 210–216 provides signals via signal lines 230 to the interface 240 at the probe output 250.

Figure 3:
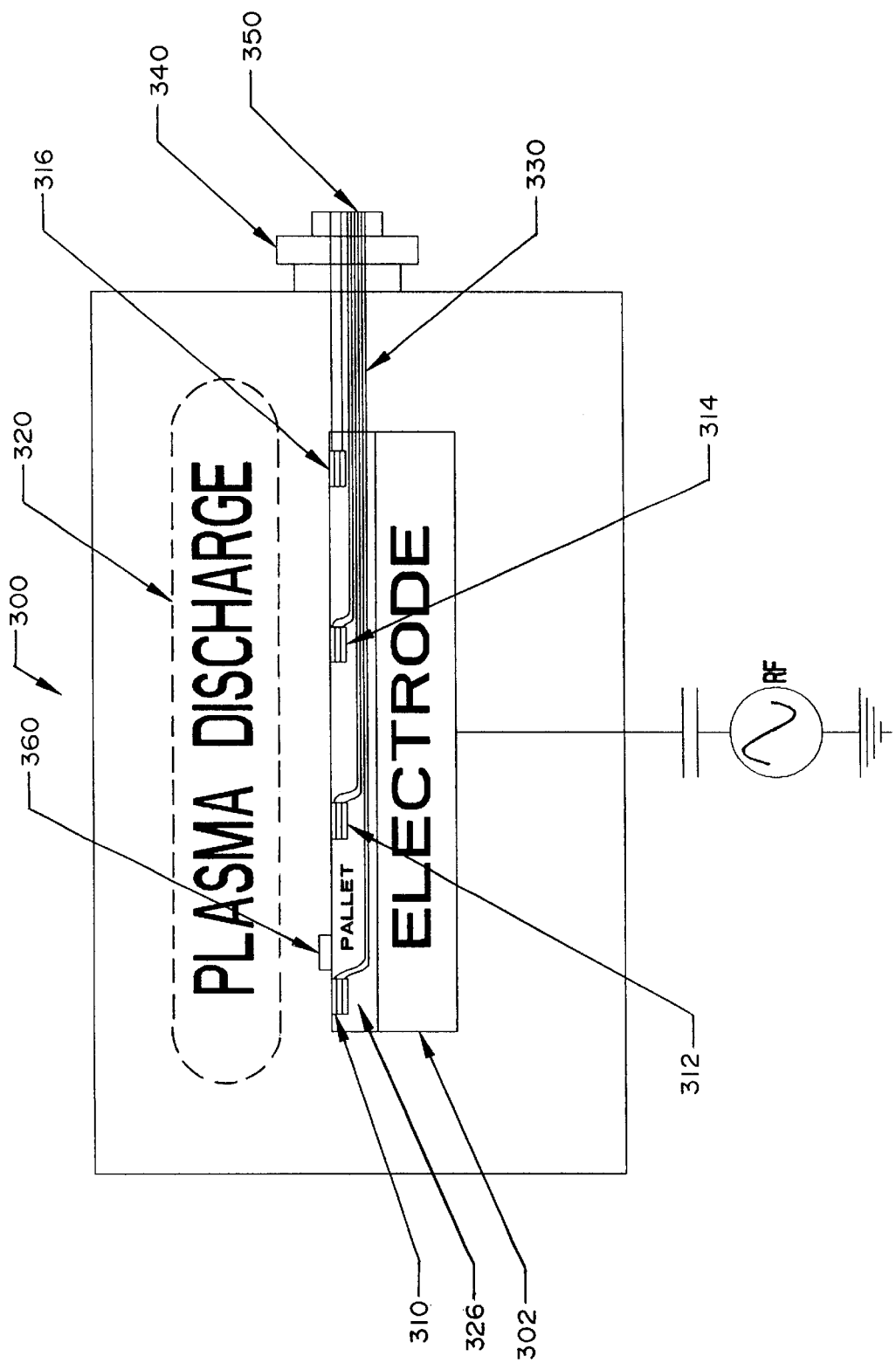
FIG. 3 illustrates a plurality of plasma electrode probes formed as part of the pallet for providing ion energy measurement and total energy impingement on the pallet surface.

FIG. 3 illustrates a plasma reactor 300 that includes a third embodiment of the present invention. In FIG. 3, a plurality of plasma electrode probes 310–316 are formed as part of a pallet 326 over electrode 302 for providing ion energy measurement and total energy impingement on the surface of the pallet 326. Again each probe 310–316 provides signals via signal lines 330 to the interface 340 at the probe output 350. A work piece 360 that is to be processed, e.g., etched, is disposed at a position on the pallet 326. The plasma electrode probes 310–316 may be formed as one of a plurality of rows of parts to be processed. For example, the plasma electrode probes 310–316 may be formed as one of a plurality of slider rows at the wafer level. Further, to minimize the ion/plasma electrical potential disruption in the plasma chamber environment, the plasma electrode probes 310–316 may be formed using a substance that is substantially identical to the material which the part being processed is composed of, e.g., the probes may be composed of silicon, silicon oxide, $Al_2O_3/TiC$ (N58), ceramics, etc.

For any plasma deposition or etching process, the associated rate will be determined by the ion flux and the ion energy distribution. For example, ion processes may be used in the manufacture of substrates for air bearing surface, for the patterning of sliders for magnetoresistive head, or for Diamond-Like Carbon (DLC) slider overcoat film deposition in computer information storage applications. The direct and simultaneous monitoring of the ion flux and the ion energy distribution allows a significant improvement in process control. After appropriate calibration measurements, the deposition or etching rate can be monitored as the plasma strength fluctuates during a run, and the run can be ended at the appropriate time. The run can in fact be defined as the duration of a specified number of ion strikes per unit of surface area, and as a function of their energy distribution. This is a significant improvement over the simple timing of deposition/etching runs.

FIG. 4 is a flow chart 400 of the method for in-situ monitoring of ion energy distribution for endpoint detection according to the present invention. At least one capacitance sensor is provided within a plasma reactor at a first position 410. Ion flux from an ion beam emanating from a plasma within the plasma reactor is detected using the capacitance sensor 420. Then, an ion flux measurement signal is generated from the capacitance sensor in response to the detection of the ion flux 430. From the ion flux measurement signal the ion distribution form the plasma may be measured. An electric potential may be applied to a capacitance sensor to tune to a predetermined energy range. The electric potential may be scanned to select various energy levels and to determine an energy distribution of the ions.

As mentioned above, the PEP can be formed in the same shape of most parts (slider and rows for magnetic recording heads and disk, silicon wafers . . . etc . . . ) that are etched or used as substrates in plasma processes. Additionally, the surface layer (or additional layers) can be composed of material identical (or similar) to the sample being etched in the chamber to minimize variation in the plasma environment. In this way, the PEP can be inserted just as a regular part without disturbing the plasma processing. Each PEP requires two electrical leads for the application and measurement of the potential difference across the capacitor and can be feed through to the external environment for measurement and monitor.

The foregoing description of the exemplary embodiment of the invention has been presented for the purposes of illustration and description. It is not intended to be exhaustive or to limit the invention to the precise form disclosed. Many modifications and variations are possible in light of the above teaching. It is intended that the scope of the invention be limited not with this detailed description, but rather by the claims appended hereto.

What is claimed is:

1. A plasma endpoint probe comprising at least one capacitance sensor disposed inside a plasma reactor at a first position for detecting ion flux emanating from a plasma within the plasma reactor that strikes a surface of the capacitance sensor inside the plasma reactor and generating an ion flux measurement signal in response to the detection of the ion flux.

2. The plasma endpoint probe of claim 1 wherein the measurement signal is provided outside the plasma reactor for processing.

3. The plasma endpoint probe of claim 2 wherein each of the at least one capacitance sensor is coupled to signal lines for routing an ion flux measurement signal outside the plasma reactor.

4. The plasma endpoint probe of claim 1 wherein the at least one capacitance sensor comprises two conductors separated by at least one insulation layer.

5. The plasma endpoint probe of claim 4 wherein the insulation layer comprises a dielectric material.

6. The plasma endpoint probe of claim 4 wherein the signal lines are coupled to the two conductors.

7. The plasma endpoint probe of claim 1 wherein the at least one capacitance sensor comprises a plurality of capacitance sensors formed as one of a plurality of rows of parts to be processed.

8. The plasma endpoint probe of claim 1 wherein the at least one capacitance sensor is formed using a substance that is substantially identical to a part being processed minimizing an ion/plasma electrical potential disruption in the plasma reactor.

9. The plasma endpoint probe of claim 1 wherein the at least one capacitance sensor is disposed in a pallet, the pallet providing support to a device being subjected to the plasma.

10. The plasma endpoint probe of claim 1 wherein the ion flux measurement signal represents a number of ions impinging a capacitance sensor.

11. The plasma endpoint probe of claim 10 wherein at least one capacitance sensor comprises a plurality of capacitance sensors diffused within the electrode.

12. The plasma endpoint probe of claim 11 wherein the plurality of capacitance sensors measure the ion distribution from the plasma.

13. The plasma endpoint probe of claim 1 wherein the at least one capacitance sensor comprises a shape of a part to be processed to prevent a disturbance of the plasma by minimizing an ion flux and an ion energy distribution in a plasma environment.

14. The plasma endpoint probe of claim 1 wherein the at least one capacitance sensor has an electric potential applied thereto for tuning the capacitance sensor to a predetermined energy range.

15. The plasma endpoint probe of claim 14 wherein the electric potential is scanned to determine an energy distribution of the ions.

16. A method for probing a plasma reactor to determine an ion flux and ion energy distribution for a plasma process, comprising:

providing at least one capacitance sensor inside a plasma reactor at a first position;

detecting ion flux emanating from a plasma within the plasma reactor that strikes a surface of the capacitance sensor inside the plasma reactor; and generating an ion flux measurement signal from the capacitance sensor in response to the detection of the ion flux.

17. The method of claim 16 wherein the at least one capacitance sensor comprises two conductors separated by at least one insulation layer.

18. The method of claim 17 wherein the insulation layer comprises a dielectric material.

19. The method of claim 17 wherein the signal lines are coupled to the two conductors.

20. The method of claim 16 wherein providing at least one capacitance sensor comprises providing a plurality of capacitance sensors formed as one of a plurality of rows of parts to be processed.

21. The method of claim 16 wherein the at least one capacitance sensor is disposed in a pallet, the pallet providing support to a device being subjected to the plasma.

22. The method of claim 16 wherein the ion flux measurement signal represents a number of ions impinging a capacitance sensor.

23. The method of claim 22 wherein at least one capacitance sensor comprises a plurality of capacitance sensors diffused within the electrode.

24. The method of claim 23 further comprising measuring the ion distribution from the plasma using the plurality of capacitance sensors.

25. The method of claim 16 further comprising preventing the disturbance of the plasma by forming the at least one capacitance sensor in a shape of a part to be processed to minimize an ion flux and an ion energy distribution in a plasma environment.

26. The method of claim 16 further comprising tuning the capacitance sensor to a predetermined energy range by applying an electric potential to the at least one capacitance sensor.

27. The method of claim 26 further comprising scanning the electric potential to determine an energy distribution of the ions.

28. The method of claim 16 further comprising forming the at least one capacitance sensor using a substance that is substantially identical to a part being processed minimizing an ion/plasma electrical potential disruption in the plasma reactor.

* * * * *

UNITED STATES PATENT AND TRADEMARK OFFICE
CERTIFICATE OF CORRECTION

PATENT NO. : 6,326,794 B1 Page 1 of 1
DATED : December 4, 2001
INVENTOR(S) : Lundquist et al.

It is certified that error appears in the above-identified patent and that said Letters Patent is hereby corrected as shown below:

<u>Title page,</u>
Item [56], FOREIGN PATENT DOCUMENTS, "07130809 5/1995 EP" should read
-- 07130809 5/1995 JP --

Signed and Sealed this

Nineteenth Day of August, 2003

JAMES E. ROGAN
*Director of the United States Patent and Trademark Office*